United States Patent [19]
Juranas et al.

[11] Patent Number: 5,711,917
[45] Date of Patent: *Jan. 27, 1998

[54] LABORATORY REACTOR APPARATUS

[75] Inventors: David L. Juranas, Bahama; Donald D. Munn; Harry A. Anderson, both of Raleigh, all of N.C.

[73] Assignee: Tecan U.S., Research Triangle Park, N.C.

[*] Notice: The term of this patent shall not extend beyond the expiration date of Pat. No. 5,709,840.

[21] Appl. No.: 665,959

[22] Filed: Jun. 17, 1996

Related U.S. Application Data

[63] Continuation-in-part of Ser. No. 584,660, Jan. 11, 1996.
[51] Int. Cl.$^6$ .................................................. B01L 3/00
[52] U.S. Cl. ....................... 422/99; 422/58; 422/100; 422/101; 422/102; 422/103; 422/104; 436/167; 436/177; 210/798; 210/808
[58] Field of Search .......................... 422/58, 99, 100, 422/101, 102, 103, 104; 436/167, 177; 210/798, 808

[56] References Cited

U.S. PATENT DOCUMENTS

| | | | |
|---|---|---|---|
| 3,875,012 | 4/1975 | Dom et al. | 206/222 X |
| 4,168,394 | 9/1979 | Yuey | 174/151 |
| 4,482,159 | 11/1984 | Ishitani et al. | 277/3 |
| 4,605,536 | 8/1986 | Kuhnert et al. | 422/99 |
| 4,787,988 | 11/1988 | Bertoncini et al. | 210/808 |
| 4,956,298 | 9/1990 | Diekmann | 430/311 |
| 5,037,549 | 8/1991 | Ballies | 210/515 |
| 5,045,193 | 9/1991 | Pinon et al. | 210/232 |
| 5,061,450 | 10/1991 | Aoyagi | 422/101 |
| 5,133,561 | 7/1992 | Hattori et al. | 277/3 |
| 5,236,666 | 8/1993 | Hulette et al. | 422/65 |

OTHER PUBLICATIONS

Promotional Brochure by Tecan entitled "A new concept in Robotic Sample Processing" Jan., 1995.

*Primary Examiner*—Harold Y. Pyon
*Attorney, Agent, or Firm*—Olive & Olive, P.A.

[57] ABSTRACT

A laboratory reactor apparatus includes a suction tube, at least a portion of which has a constricted inside diameter. The lower portion of the suction tube is sealed to a sintered frit filter medium. The suction tube mounts in a reactor block into a reactor vial for receiving chemical components. An inlet channel with a first seal is formed through the block and conveys chemical component materials to the vial, and a suction channel with a second seal, coaxial with the suction tube, is used to remove resultant chemical compound materials therefrom. A pressurized gas channel containing inert gas is formed through the block to intersect the suction channel and the inlet channel.

8 Claims, 7 Drawing Sheets

LABORATORY REACTOR APPARATUS

RELATED APPLICATION

This application is a Continuation-In-Part of co-pending patent application Ser. No. 08/584,660, filed Jan. 11, 1996.

BACKGROUND OF THE INVENTION

1. Field of the Invention

This invention relates to an apparatus for use in the automatic mechanized combining of chemical components and the synthesis and evaluation of chemical compounds produced thereby, and more particularly to a reactor block and suction tube for use in removing liquid from a reactor vessel of such apparatus.

2. Description of the Related Art

The teachings of prior filed application Ser. No. 08/584,660 are incorporated herein by reference.

In the process of automatically introducing and reacting chemical components for the purpose of generating new and useful chemical compounds, utilizing robotic systems such as the GENESIS# processor, supplied by Tecan US, Inc., Research Triangle Park, N.C., a suction tube is positioned for extracting the resultant compound from a reactor vessel. The chemical processing, primarily intended for the synthesis of peptides and pharmaceutical compounds, is controlled by a programmed computer to combine, warm and agitate the components and to extract the resultant compound. The chemical components are introduced in a slurry for reaction in the vessel. An open crystalline matrix resin is typically utilized to provide reaction sites for synthesis. The resultant molecules are chemically cleaved off the resin matrix for removal from the vessel.

In the prior art, the reaction chamber is typically a cavity formed within a TEFLON® reactor block. A sealing membrane, or septum, is affixed to the block to seal the top of the chamber. The bottom of the chamber is covered with a glass frit that allows the solvent to pass through to the bottom of the chamber, leaving the resin within. A serpentine tube is attached to each chamber below the glass frit and extends upwardly to a height comparable to the top of the chamber and back down to the bottom of the block. The serpentine tubing serves as a trap, or valve, to prevent the solvent from draining out of the chamber. In the prior art, a transverse channel is machined into the block to connect a common pressurized inert gas source to all the chambers. When gas is introduced and pressure is applied (2–3 lb/in$^2$), the liquid in the reaction chamber is forced through the frit and lower tubing, simultaneously evacuating all chambers of liquid, but leaving the resin within the chamber.

In the suction tube of the invention as well as that of the prior art, a sintered glass frit is fused in sealed relation to the lower end of the suction tube to act as a filter to separate the resin crystals and remove the fluid from the flask. However, as a matrix of glass beads and interstitial cavities, the frit tends to act as a capillary when immersed into the liquid in the flask. As more fully described below, this capillary action tends to occlude the frit and upset the fluid control required in the reactor system, causing operational difficulties and distorted evaluations. In particular, when fluid is added to the flask from an inlet tube, due to the saturated frit, fluid rises in the suction tube to become isolated from the rest of the reaction material.

It is therefore an object of this invention to provide a laboratory reactor apparatus combining a reactor vessel in sealed contact with an inlet channel and a suction tube such that the suction tube is free of fluid until a vacuum is applied.

It is an additional object of this invention to provide an improved seal for the inlet and outlet tubes of such reactor vessel to prevent leakage.

It is a further object of this invention to provide a reactor apparatus which permits evacuation of resultant chemical products from each such reactor vessel independent of other such flasks.

Other objects and advantages will be more fully apparent from the following disclosure and appended claims.

SUMMARY OF THE INVENTION

The invention provides an improved reactor apparatus having a detachably mounted reactor vessel and sealingly connected inlet and outlet channels. A reactor block for mounting the reactor vessel has an angular inlet channel and a linear outlet channel mounting a suction tube connected to the vessel. Each of the inlet and outlet channels is sealed by means of a chamber filled with pressurized gas to prevent leakage to atmosphere. The suction tube for extracting the resultant chemical compound from the reactor vessel fits snugly within the outlet channel formed by a bore in the reactor block. The suction tube also has a vent hole at a level and location which allows pressure created in the reactor vessel to escape up the suction tube and out the vent hole to equalize in the bore adjacent the suction tube in the outlet channel.

DETAILED DESCRIPTION OF THE INVENTION AND PREFERRED EMBODIMENTS THEREOF

The invention disclosed in prior application Serial No. 08/584,660 provides an improved reactor block and reactor vial or vessel for use in automated chemical synthesis over those previously known in the art. The invention disclosed herein further provides a highly developed suction tube for use in conjunction with the reactor apparatus.

Figure 1:
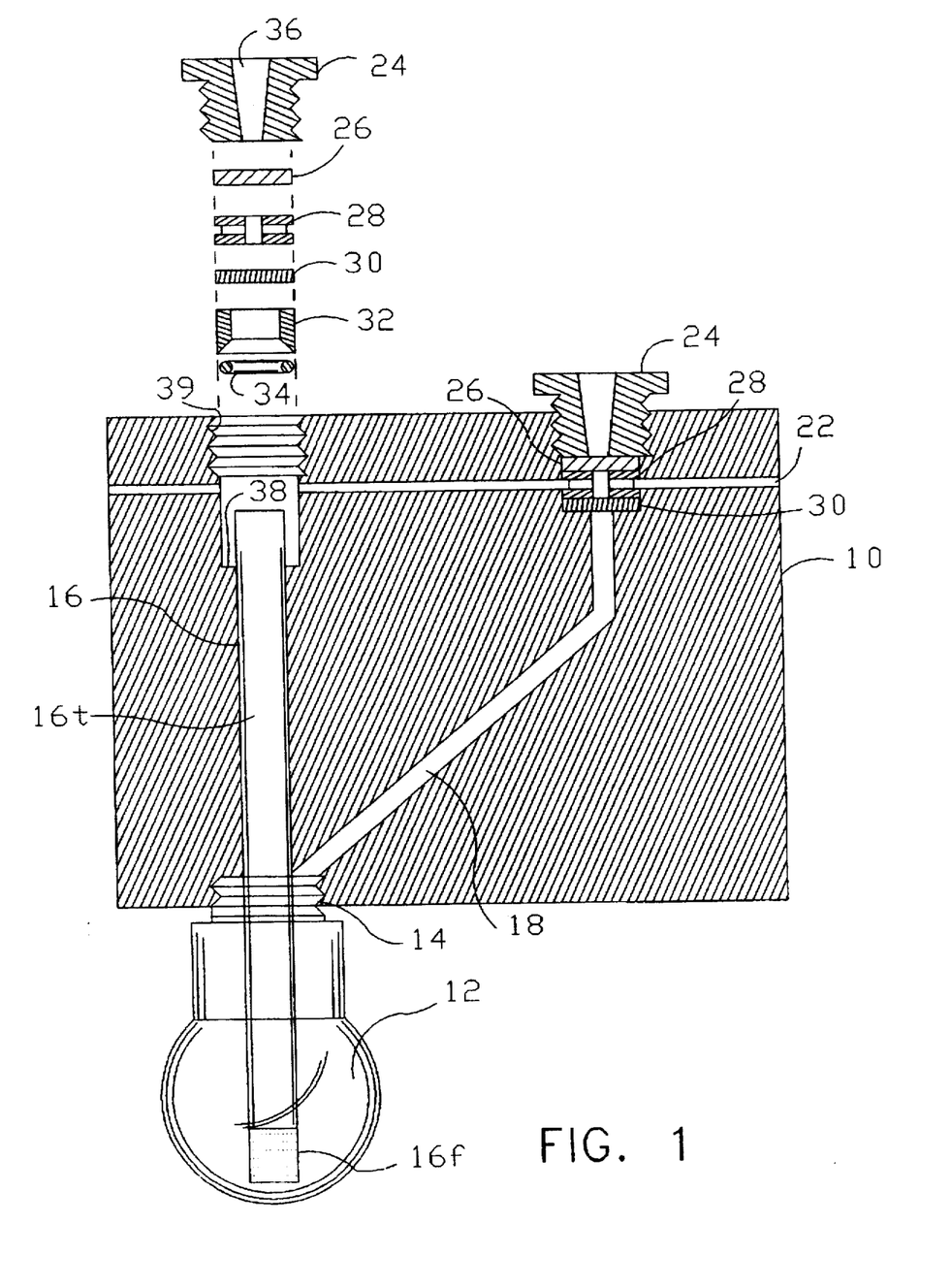
FIG. 1 is a front elevation cross section of a reactor block of the earlier patent application with a known reactor vessel or vial and suction tube (not in cross section) connected thereto and with the sealing components of the suction tube portion shown in exploded relation for clarity.
Figure 2:
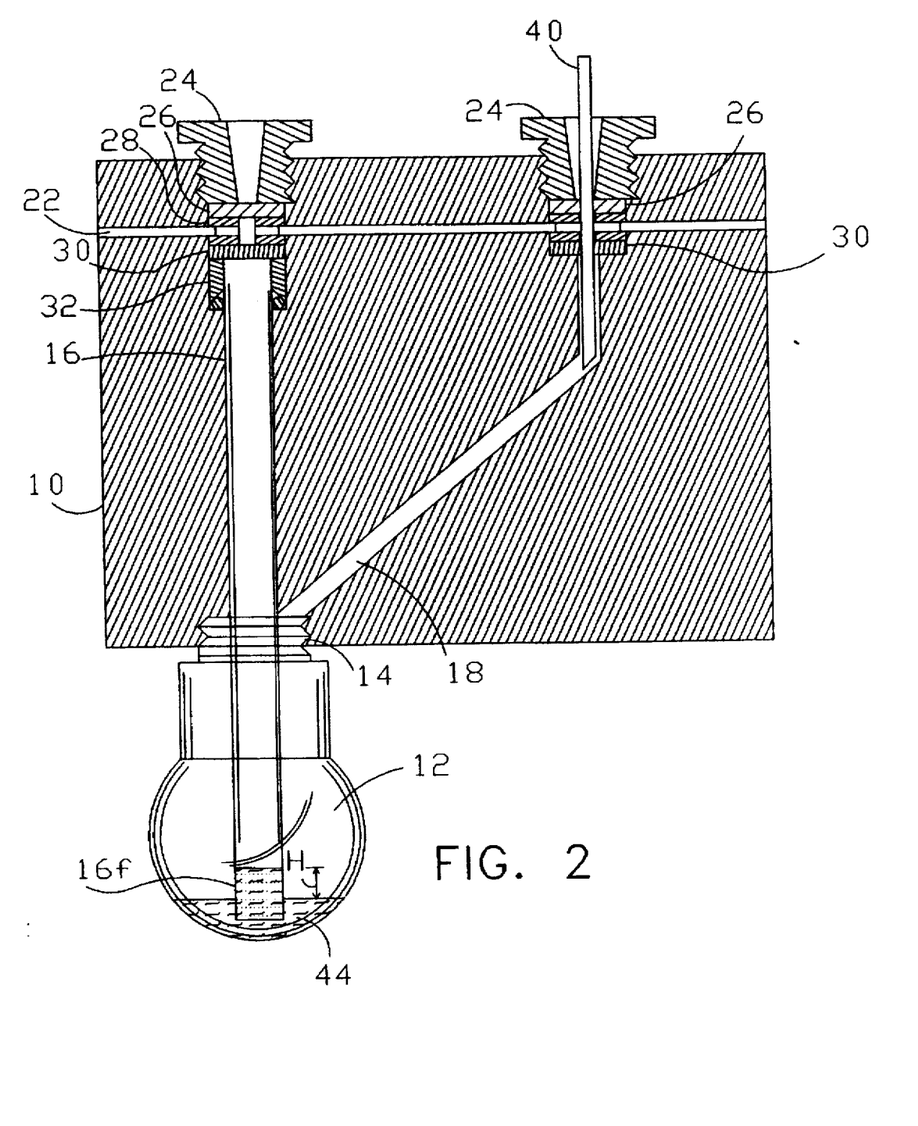
FIG. 2 illustrates the reactor apparatus of FIG. 1 with a liquid in the reactor vial rising by capillary action in the frit portion of the suction tube.
Figure 3:
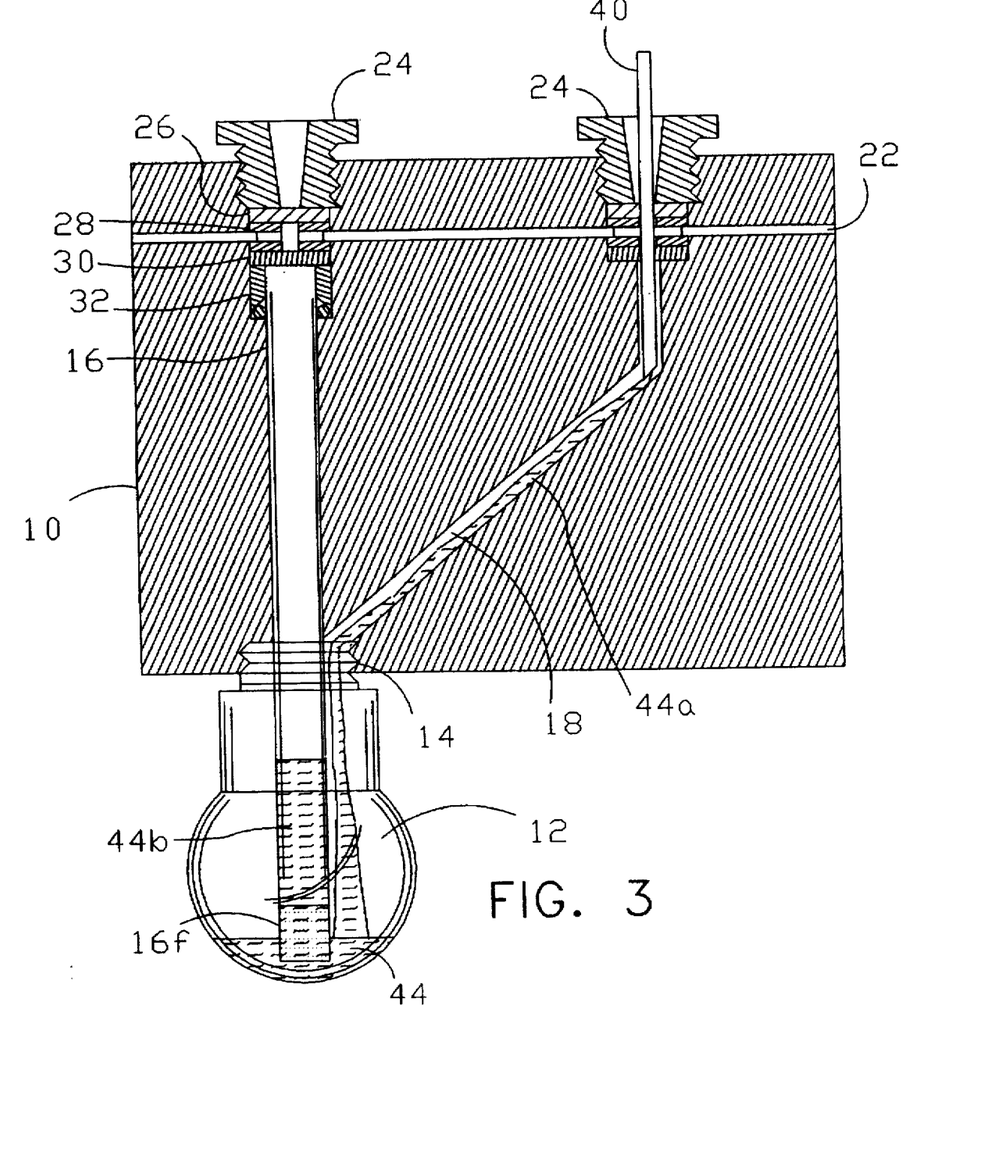
FIG. 3 illustrates the reactor apparatus of FIG. 2 with additional liquid flowing into the reactor vial and being forced up into the suction tube.

FIGS. 1–3 depict a preferred embodiment of the invention of the earlier application. As shown in FIG. 1, suction channel 16 is formed so as to pass from an upper end to a lower end of reactor block 10 and has an enlarged upper portion with shoulder 38 and internal closure threads 39. Inlet channel 18 is formed through block 10 with its upper portion substantially parallel to and laterally offset from suction channel 16 and a lower portion at an angle so that the lower extremity of inlet channel 18 intersects suction channel 16 near its lowest point in reactor block 10. Vial-engaging threads 14 are formed within an enlarged lower portion of suction channel 16 to receive a reactor vial 12 and also accommodate the lower end of the angled lower portion of inlet channel 18. Reactor block 10 is preferably formed of a substantially inert material, such as stainless steel or TEFLON®, depending primarily on the chemicals to be encountered.

Gas channel 22 is formed through reactor block 10 in an orientation to intersect an enlarged upper portion of inlet channel 18 and the enlarged upper portion of suction channel 16. In operation, gas channel 22 is filled with a low-reactivity gas, such as nitrogen or argon, under pressure. A flow-restrictive valve (not shown) is connected to an outlet end of gas channel 22 so as to maintain pressure therein. Suction tube 16t, having a filtration medium 16f, such as, for example, a sintered glass frit at its lower end, is inserted snugly into suction channel 16 with its upper end residing above shoulder 38. Reactor vial 12 is assembled to the lower portion of suction channel 16 by means of screw threads 14 to enclose sintered glass frit 16f.

The elements shown in exploded relation in FIG. 1, act to secure and seal suction tube 16t into reactor block 10. An annular sealing member 34, e.g. an "o" ring, is placed snugly over the outer diameter of suction tube 16t to be in contact with substantially planar shoulder 38. Pressure washer 32, having an axial channel passing from an upper planar end and terminating at a lower end as an internally conical cavity, is placed so as to engage the upper portion of sealing member 34. A lower sealing member, such as lower septum 30, being substantially impervious to liquid passage, is next placed upon pressure washer 32. Lower septum 30 is preferably formed of a penetrable laminated sheet having a lower layer of a low reactivity polymer, e.g. TEFLON®, and an upper layer of a resilient polymer, e.g. silicone.

Figure 8:
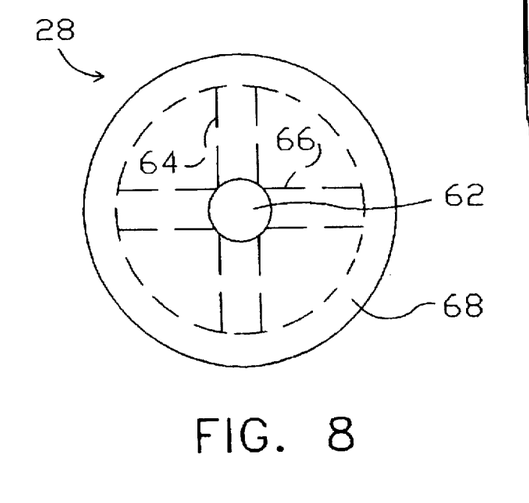
FIG. 8 is an enlarged top plan view of a spacer formed with gas flow channels for use in the apparatus of the present invention as well as in the apparatus of the invention of the prior patent application.

Spacer 28, shown in detail in FIG. 8, is assembled on lower septum 30, with upper septum 26 placed thereupon. Spacer 28, as shown in FIG. 8, is disc-shaped with a pair of parallel, planar surfaces. An axial bore 62 passes perpendicularly through spacer 28 and a pair of diametral bores 64, 66 are formed to be mutually perpendicular and along a pair of axes in a plane substantially parallel to and between the planar surfaces of spacer 28. A channel 68 is formed to be open around the circumference of spacer 28. Bores 62, 64, 66 and channel 68 are mutually connected. When spacer 28 is assembled into the apparatus of the invention, gas channel 22 is in fluid communication with diametral bores 64, 66 by way of circumferential channel 68 to establish a pressure in axial bore 62 for sealing lower septum 30 against leakage. Upper septum 26 is of a similar laminate and similar orientation, being substantially parallel to lower septum 30. Plug 24, having an internal conical entry 36 vertically formed through its center and external threads is releasably attached into internal threads 39, applying sealing pressure to components 26, 28, 30, 32 and 34 described above.

When plug 24 is assembled with the sealing components as discussed above, spacer 28 resides so as to be substantially vertically centered on gas channel 22. According to the detail of spacer 28 shown in FIG. 8, central bore 62 aligns with entry 36 of plug 24 and the inside diameter of suction tube 16t. Perpendicularly related diametral bores 64 and 66 intersect central bore 62, and circumferential channel 68 is formed at the outer diameter of spacer 28 to connect the outer ends of bores 64 and 66. When assembled into reactor block 10 as described above, a pressurized gas in gas channel 22 enters circumferential channel 68 and through diametral bores 64, 66 establishes a pressure in the enclosed chamber so as to prevent leakage of chemical components through the respective upper and lower septa 26, 30.

The upper end of inlet channel 18 is sealed with a similar septum 30, spacer 28, septum 26 and plug 24. Thus assembled, reactor vial 12, inlet channel 18, suction channel 16 and suction tube 16t comprise a substantially sealed environment.

In FIG. 2, the sealing components which were illustrated in exploded relation in FIG. 1 are shown in their assembled position. A hollow injecting needle 40 is inserted into inlet channel 18, piercing through flexible septa 26, 30. A small amount of reactive slurry 44, comprising a chemical reactant suspended in a liquid, is shown within reactor vial 12. Sintered glass frit 16f extends from within slurry 44 to a distance H above the surface of slurry 44. Frit 16f is saturated with the liquid component of slurry 44 to height H due to the capillary action of the sintered glass matrix. The solid or semi-solid components of slurry 44 are filtered out by sintered glass frit 16f.

According to FIG. 3, as additional slurry 44a is injected to the sealed system through needle 40, the additional pressure created causes the liquid component of the slurry to rise within suction tube 16t by passing through saturated frit 16f. Chemical materials slurry 44b enclosed in suction tube 16t above frit 16f are isolated from the balance of the system which is in reactor vial 12, thus forming a separate, and less controllable, reactive environment. In practice, the material of which septa 26, 30 is made does not maintain a complete seal once it has been pierced by injecting needle 40. When lower septum 30 has been pierced, needle 40 is removed, and the gas is maintained under pressure in gas channel 22, some of the pressurized gas infiltrates inlet channel 18 forcing the liquid of slurry 44 farther up suction tube 16t.

In order to keep all chemical components together and in balance during the reaction cycle and thus exposed to common thermal and physical actions, improvements over the teachings of the prior application are next described as illustrated in FIGS. 4, 6, 7 and 9. A major element of the present invention is suction filtration tube 50, shown in detail in FIG. 4, which is used in conjunction with a suction needle 60 of FIG. 5. Suction tube 50 has an upper portion 52 with an inside diameter which is substantially larger than diameter D of suction needle 60 (FIG. 5). Upper portion 52 is connected coaxially to constricted portion 54 having an inside diameter B sufficient to slidingly receive the lower portion of suction needle 60. Whereas the inside diameter of upper portion 52 is somewhat large in the preferred embodiment, the invention recognizes that tube 50 would function according to the principles and objectives set out above with a constricted inside diameter throughout its length, such as diameter B. Constricted portion 54 is in turn connected coaxially to a filtration element, sintered glass frit 50f. Upper portion 52 is preferably substantially equal in its inside and outside diameters to the respective diameters of previously discussed suction tube 16t of FIGS. 1–3. A vent hole 56 of any convenient diameter is formed radially through the wall of full inside diameter portion 52. The outer diameter of constricted portion 54 may be similar to or different than the outside diameter of full inside diameter portion 52. Constricted inside diameter B is formed to be minimally greater than the outer diameter D of suction needle 60 (FIG. 5), nominally 0.1 mm (0.004 inch). Frit 50f is formed with a nominal pore size in the range of 70–100 μm. Suction needle 60 has concentric tubes with individual ports 61, 63 and respective lumen ports 61', 63'.

Figure 4:
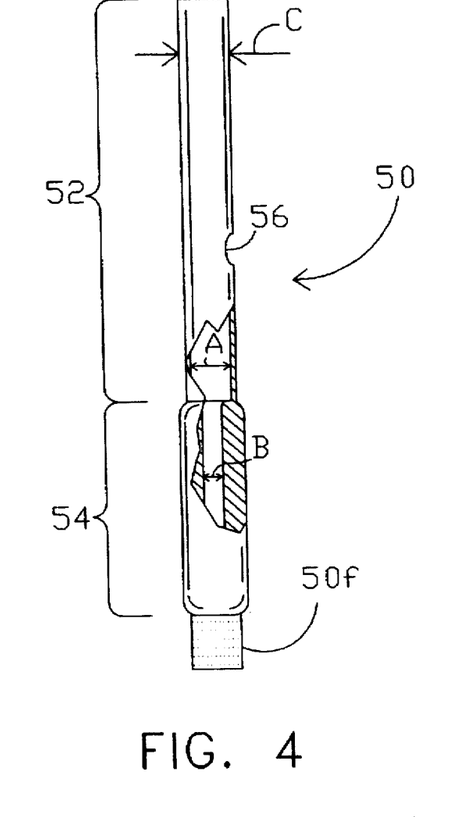
FIG. 4 is a front elevation view of a suction tube of the invention in which a segment of a constricted bore portion thereof is broken away for clarity.
Figure 5:
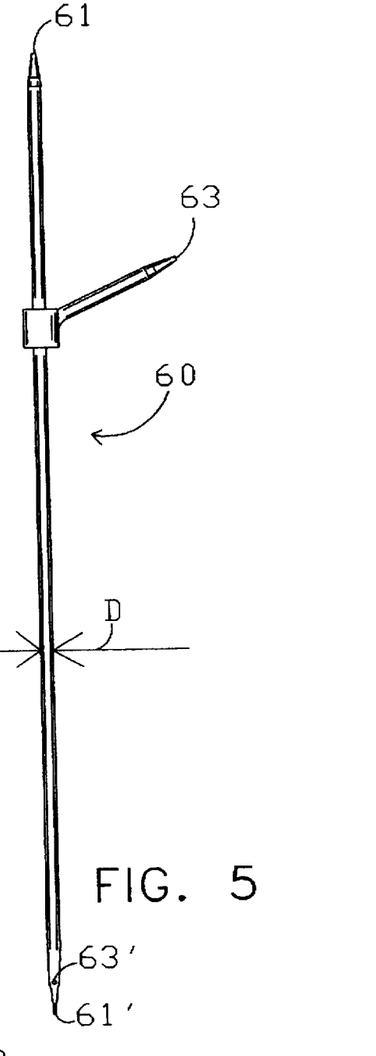
FIG. 5 is a front elevation view of a known fluid extraction needle used in conjunction with the invention.
Figure 6:
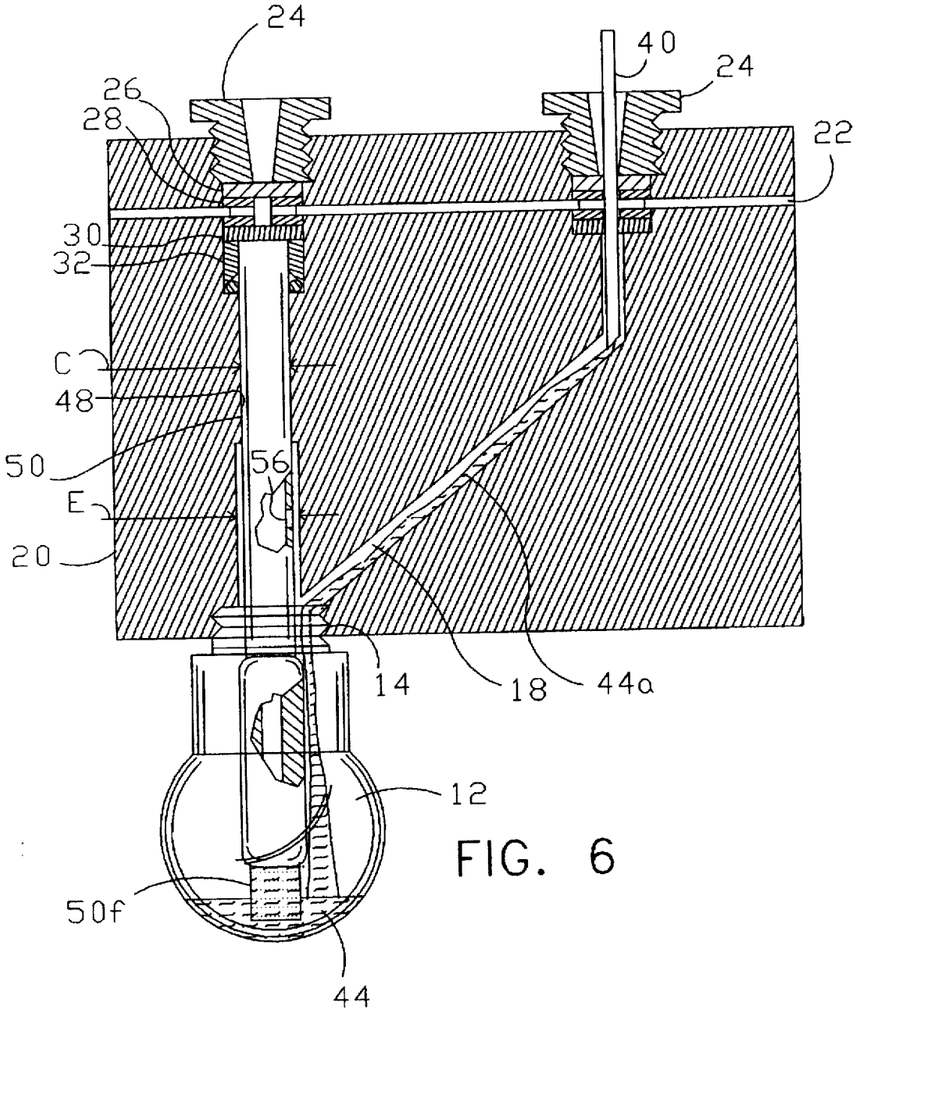
FIG. 6 is a front elevation view of a reactor block of the invention with a known reactor vial and a suction tube of FIG. 4 having a segment thereof broken away to show a vent hole and with additional liquid flowing into the reactor vial and not rising in the suction tube.

The illustration of the invention in FIG. 6 corresponds to the earlier discussed apparatus of FIG. 3, including a particular modification to reactor block 10 of (FIG. 3) and improved suction tube 50 (see FIG. 4). As opposed to previously discussed reactor block 10 (FIG. 3), having suction channel 16 which, throughout its length, snugly receives suction tube 16t, improved reactor block 20 is formed with suction channel 48 at a diameter C in its upper portion which will snugly receive and firmly hold suction tube 50. The lower portion of suction channel 48 is of a diameter E sufficient to maintain clear space around the outer diameter C of suction tube 50 for pressure equalization. The length of upper portion 52 is adequate to pass downward from lower septum 30 to within reactor flask 12, as the described components are assembled. Upper septum 26 is mounted on block 20 in parallel relation to lower septum 30 at a separation distance so as to communicate with gas channel 22. Inert gas passes under pressure between upper and lower septa 26, 30 which serve as sealing means to prevent leakage of the chemical components after the septa have been penetrated.

Figure 9:
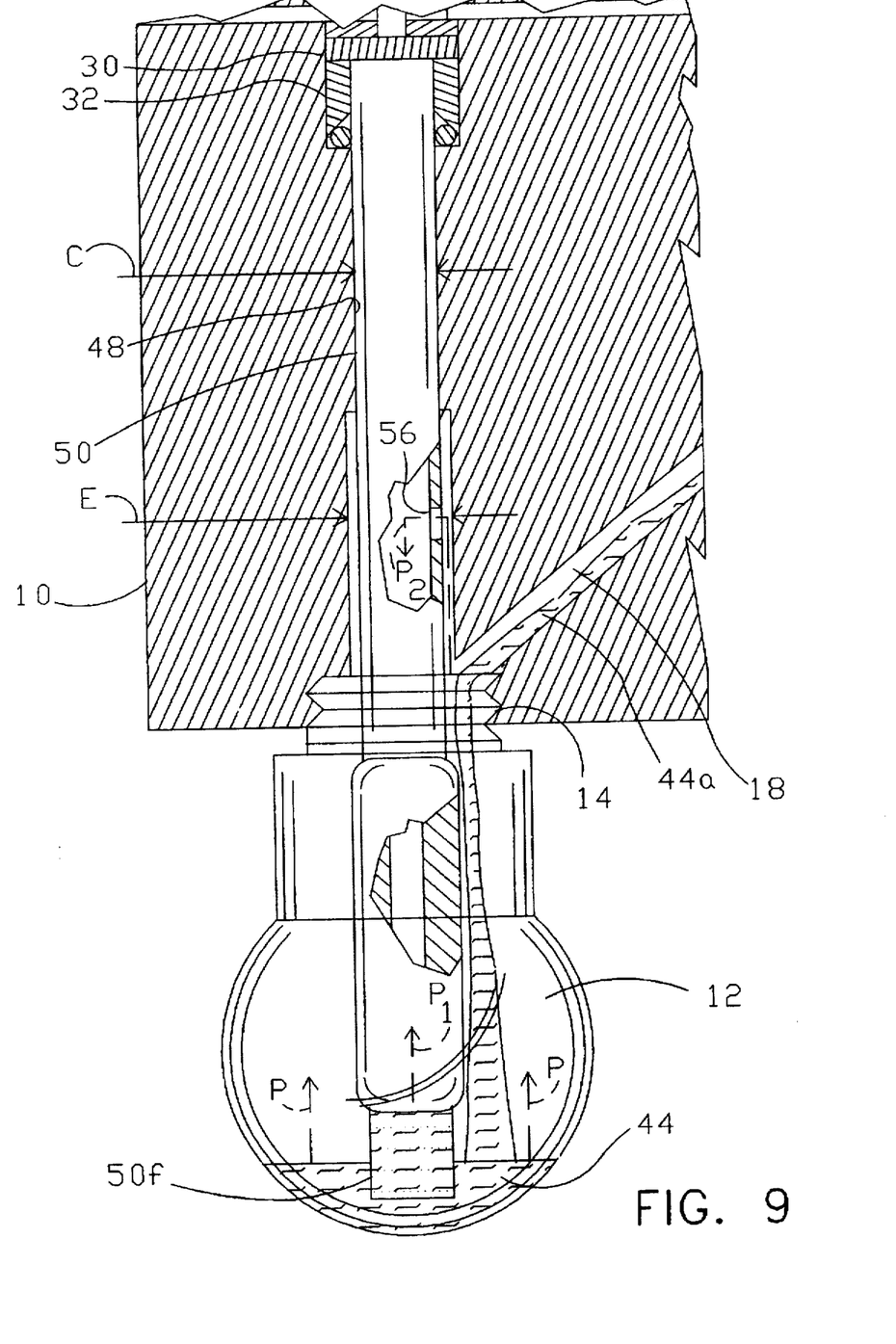
FIG. 9 is an enlarged view of a portion of FIG. 6 with the addition of fluid pressure-indicating arrows for purposes of discussion.

As seen in FIG. 6, hollow injecting needle 40 has penetrated both upper and lower septa to enter inlet channel 18. Slurry 44a is flowing through inlet channel 18 to become slurry 44 within reactor vial 12. Frit 50f is saturated with capillarily drawn liquid, but no liquid is contained in the portions of suction tube 50 above frit 50f. FIG. 9 is an enlarged view of the significant portion of FIG. 6 illustrated for greater detail. As slurry 44a flows into reactor vial 12 (or gas under pressure infiltrates through a perforated septum, as discussed above), upwardly directed pressure P is generated above the surface of slurry 44. This pressure is carried through saturated frit 50f, as indicated by arrow $P_1$. Simultaneously, the pressure generated above slurry 44 is transmitted through the space around suction tube 50 and within suction channel 48 to enter vent hole 56 as indicated by arrow $P_2$. Pressure $P_1$ and pressure $P_2$ are equal in magnitude and opposite in direction, resulting in equilibrium. Thus, a pressure balance is effected by the vented suction tube 50 together with the increased size of suction channel 48 during flow of fluid or leak of pressure into reactor vial 12.

Figure 7:
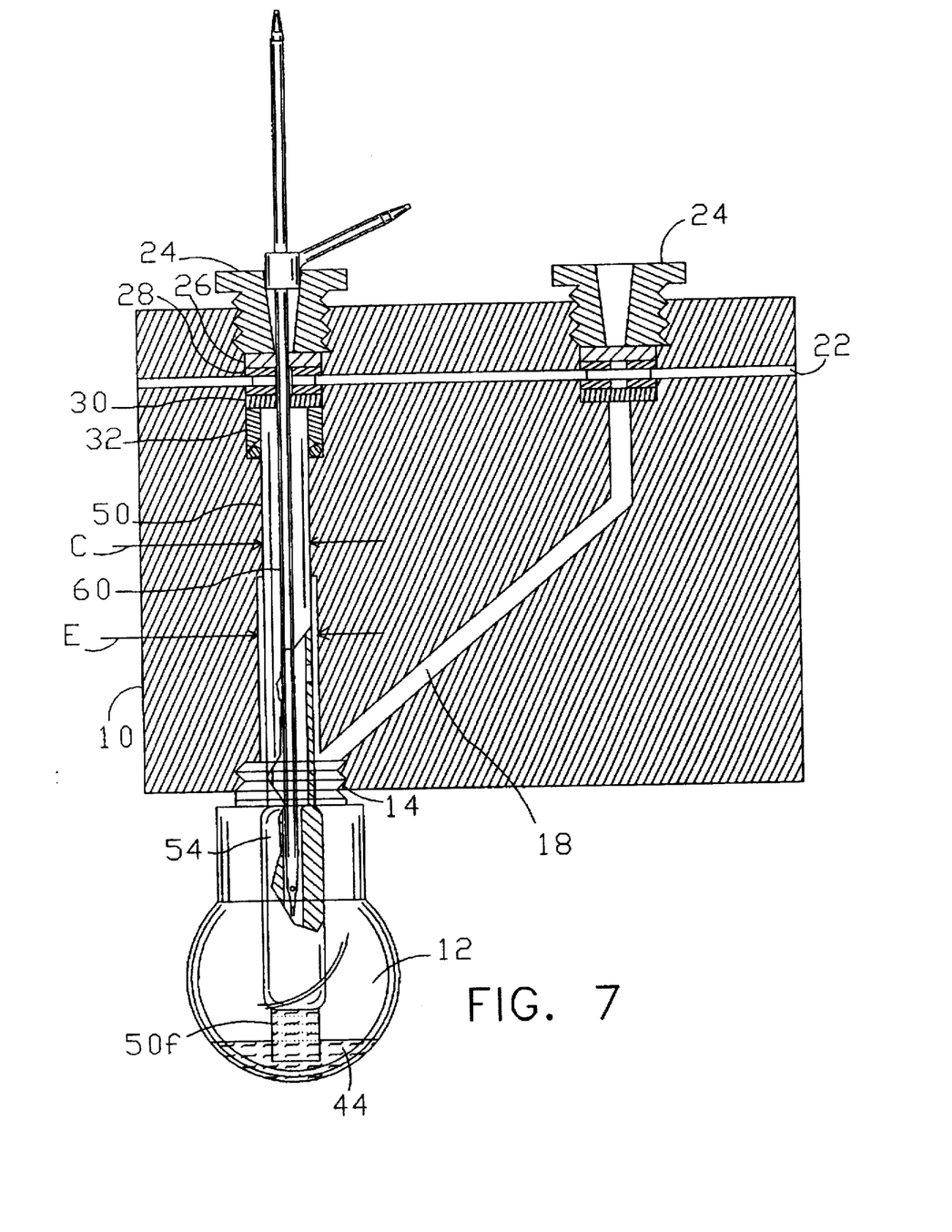
FIG. 7 illustrates the reactor apparatus of FIG. 6 with the extraction needle of FIG. 5 inserted slidingly within the narrow bore of the suction tube.

The suction needle 60, described above in relation to FIG. 5, is shown in FIG. 7 inserted into suction tube 50 through upper septum 26 and parallel lower septum 30 in position to remove a resultant chemical compound from reactor vial 12. As suction needle 60 is passed through constricted portion 54 of suction tube 50, the minimal diametral space is sufficiently small to achieve a capillary seal and thus prevent drawing gas into needle 60 under vacuum. Suction needle 60 incorporates dual lumens, one of which allows entry of air or other gas, thus enabling a pressure equalization during removal of chemical product through the second lumen under vacuum.

While the invention has been described with reference to specific embodiments thereof, it will be appreciated that numerous variations, modifications, and embodiments are possible, and accordingly, all such variations, modifications, and embodiments are to be regarded as being within the spirit and scope of the invention.

What is claimed is:

1. Apparatus for chemical synthesis comprising:
   (a) a reactor block with a first channel and a second substantially straight channel each channel passing through said block from an upper block surface to a lower block surface, said second channel having a first inside diameter at a first end and a second inside diameter different than said first inside diameter at a second end thereof said second end being adjacent said lower block surface;
   (b) a reactor vessel removably connected to said reactor block in fluid communication with said first and second channels;
   (c) a suction tube sized internally to slidingly receive a liquid transfer needle and sized externally to fit in said second channel and having a filtration medium connected to a lower end thereof wherein an upper end of said suction tube is received within said second channel and said lower end is positioned within said reactor vessel;
   (d) a first and a second spaced apart parallel penetrable sealing means removably mounted in said first channel wherein said first sealing means is in contact with said upper end of said suction tube; and
   (e) a third and a fourth spaced apart parallel penetrable sealing means removably said second channel.

2. The apparatus as claimed in claim 1, wherein said suction tube further comprises a vent hole passing through a side of said suction tube to communicate with said second diameter of said second channel wherein said second diameter is greater than the external size of said suction tube.

3. The apparatus described in claim 1, further comprising an annular sealing member mounted circumferentially for securing said suction tube within said passage and operative to seal said tube to said reactor block.

4. The apparatus described in claim 1, wherein said first and second channels in said reactor block converge to an intersection in fluid communication with said upper portion of said reactor vessel when connected to said reactor block.

5. The apparatus as claimed in claim 1, wherein said filtration medium is formed with a nominal pore size between 70–100 μm.

6. The apparatus as claimed in claim 1, further comprising a gas channel formed in said reactor block and connected between said first and second sealing means on one end and said third and fourth sealing means on a second end and filled with gas under pressure for preventing leakage of liquids through each said sealing means after each said sealing means has been pierced.

7. The apparatus described in claim 3, further comprising a pressure washer mounted on said sealing member and having an axial bore larger than the external diameter of said suction tube and having an internal conical cavity.

8. The apparatus described in claim 5, wherein said gas has a low reactivity with respect to chemical ingredients intended for use in said apparatus.

\* \* \* \* \*

UNITED STATES PATENT AND TRADEMARK OFFICE
CERTIFICATE OF CORRECTION

PATENT NO. : 5,711,917
DATED : January 27, 1998
INVENTOR(S) : David L. Juranas; Donald D. Munn; Harry A. Anderson It is certified that error appears in the above-indentified patent and that said Letters Patent is hereby corrected as shown below:

Column 1, line 21, correct "GENESIS#" to read --GENESIS$^{TM}$--.
(PTO error)

Signed and Sealed this

Thirtieth Day of June, 1998

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,711,917
DATED : January 27, 1998
INVENTOR(S) : David L. Juranas; Donald D. Munn; Harry A. Anderson It is certified that error appears in the above-identified patent and that said Letters Patent is hereby corrected as shown below:

In Claim 1, line 25, after "removably", insert --mounted in--.

Signed and Sealed this

First Day of December, 1998

Attest:

BRUCE LEHMAN

*Attesting Officer*     *Commissioner of Patents and Trademarks*